United States Patent [19]
Bonyhadi et al.

[11] Patent Number: 5,612,018
[45] Date of Patent: *Mar. 18, 1997

[54] DRUG SCREENING AND TREATMENT FOR HIV THYMOCYTE DEPLETION

[75] Inventors: Mark L. Bonyhadi, Belmont; Hideto Kaneshima, Palo Alto; Joseph M. McCune, San Francisco; Reiko Namikawa; Lishan Su, both of Palo Alto, all of Calif.

[73] Assignee: Systemix, Inc., Palo Alto, Calif.

[*] Notice: The term of this patent shall not extend beyond the expiration date of Pat. No. 5,476,997.

[21] Appl. No.: 183,178

[22] Filed: Jan. 18, 1994

Related U.S. Application Data

[63] Continuation-in-part of Ser. No. 882,937, May 14, 1992, abandoned, which is a continuation-in-part of Ser. No. 836,195, Feb. 13, 1992, which is a continuation of Ser. No. 347,912, May 5, 1989, abandoned.

[51] Int. Cl.⁶ .................................................. A61K 49/00
[52] U.S. Cl. .......................... 424/9.2; 424/553; 424/577; 424/580; 424/582; 800/2; 800/DIG. 2; 800/DIG. 5
[58] Field of Search .................................. 424/9, 553, 577, 424/580, 582; 800/2, DIG. 2, DIG. 5

[56] References Cited

PUBLICATIONS

McCune, Cell 64: 351–363 (1991).
McCune et al. (b), Annual Reviews in Immunology 9: 399–429 (1991).
McCune et al. (c), Science 247: 564–566 (1990).
Kaneshima et al., Nature 348: 561–562 (1990).
Namikawa et al. (a), J. Exp. Med. 172: 1055–1063 (1990).
Namikawa et al. (b), Science 242: 1684–1686 (1988).
McCune et al. (a), Science 241: 1632–1639 (1988).

*Primary Examiner*—Jasemine C. Chambers
*Attorney, Agent, or Firm*—Pamela J. Sherwood; Fish & Richardson P.C.

[57] ABSTRACT

A method is provided for screening compounds for the ability to supress thymocyte depletion in thymuses of HIV-infected individuals, particularly enhancing the $CD4^+$-expressing population as compared to an untreated individual. Particularly, drugs are provided which allow for this result, cyclosporine A being exemplary.

7 Claims, No Drawings

DRUG SCREENING AND TREATMENT FOR HIV THYMOCYTE DEPLETION

This invention was made with Government support under NIH Grant no. RO1 AI 29323. The Government has certain rights in this invention.

CROSS-REFERENCE TO RELATED APPLICATIONS

This application is a continuation-in-part of application Ser. No. 07/882,937, filed May 14, 1992, now abandoned, which is a continuation-in-part of application Ser. No. 836,195, filed Feb. 13, 1992, which is a continuation of application Ser. No. 347,912, filed May 5, 1989 now abandoned.

INTRODUCTION

1. Technical Field

The field of this invention is the screening of drugs and treatment for HIV.

2. Background

The Acquired Immunodeficiency Syndrome (AIDS) is a serious and expanding pandemic. While extraordinary efforts have been made to find ways to protect humans from its etiologic agent, the human immunodeficiency virus (HIV), to date there has been little other than palliative treatments available. For the most part, drugs have been directed to slowing the intractable course of the disease and to treating various of the opportunistic infections which often accompany it.

It is recognized that a major consequence of infection with HIV is the substantial loss of "helper" T-cells, which are identified by the CD4 marker. In the normal ratio, helper T-cells are a substantially larger population than "suppressor/cytotoxic" T-cells, which are CD8+. During the course of the disease this ratio is reversed and ultimately there are substantially no helper T-cells in the external circulation. As a result, fullblown AIDS occurs as an inevitably fatal disease.

There is therefore substantial interest in identifying procedures which may substantially slow the disease, or therapies where long-term maintenance may be achieved while allowing the diseased patient to carry on substantially normal functions.

Relevant Literature

Studies of the progression and treatment of HIV infection and AIDS can be found in Ameisen, J. C. and Capron, A., Immunology Today, (1991), 12:102–105; Yarchoan, R., et al., Blood, (1991), 78:859–884; McCune, J. M., et al., Science, (1990), 247:564–566; Yarchoan, R., et al., New Engl. J. Med., (1989), 321:726–738; Capon, D. J. and Ward, R. H. R., Ann. Rev. Immunol., (1991), 9:649–678 and McCune, J. M., Cell, (1991), 64:351–363. Background on the role of the thymus in lymphocyte development may be found in Haynes, B. F., Seminars in Immunol., (1990), 2:67–77 and Shortman, K., et al., Seminars in Immunol., (1990), 2:3–12. Further discussion of the role of the thymus in AIDS may be found in Schnittman, S. M., et al, P. N. A. S., (1990), 87:7727–7731; Schuurman, H-J., et al, Am.J-.Path., (1989), 134:1329–1338; Dupay, J-M., et al., Thymus, (1991), 17:205–218 and Pantaleo, G., et al., P.N.A.S., (1991), 88:9838–9842. Description of the SCID-hu mouse may be found in McCune, J. M., et al., Science (1988), 241:1632–1639, Namikawa, R., et al., J. Exp. Med., (1990), 172:1055–1063 and McCune, et al., Ann. Rev. Immunol. (1991), 9:395–429.

SUMMARY OF THE INVENTION

A screening method is provided for identifying drugs inhibiting thymocyte depletion in cases of HIV infection. Drugs shown to be positive may be administered to a seropositive human for HIV to provide for continued thymocyte maintenance.

DESCRIPTION OF THE SPECIFIC EMBODIMENTS

Methods are provided for the screening of compounds for their effectiveness in the maintenance of thymocytes for human hosts seropositive for HIV. The method employs a small animal model comprising an immunocompromised host into which has been implanted fetal thymus and fetal liver substantially contiguous, so as to form an interacting structure. This structure is extensively described in U.S. application Ser. No. 347,812, filed May 5, 1989.

The method comprises inoculating the implant with an infectious level of HIV and then determining the effect of the virus on T lymphopoiesis as a function of time. The T lymphopoiesis may be determined by histological or flow-cytometric-inspection of the thymus for $CD4^+$ and/or $CD8^+$ T cells or progenitors thereof, the level of CD4+ T cell population in the peripheral blood, or other indicia of T lymphopoiesis. Compounds which are found to be effective in the assay are defined as those which prevent either quantitatively or qualitatively HIV-induced suppression of T-lymphopoiesis. Such compounds may then be used in the treatment of seropositive HIV individuals to enhance thymocyte maintenance.

In conjunction with drug treatment, autologous or allogeneic T cell progenitors may be administered, e.g. intrathymically. The progenitor cells may either be totipotent hematopoietic stem cells or a progenitor cell committed to the T and/or myeloid lineage(s). Usually, about $10^3$ or more cells will be administered to reconstitute thymopoiesis in the recipient thymus.

The small animal model will be an immunocompromised mammal, particularly a combined immunodeficient mammal, more particularly a severe combined immunodeficient mammal. These mammals are characterized by their lack of functional T cells, which may be as a result of any of a large number of defects associated with the ability of an hematopoietic progenitor cell to differentiate and mature to a mature T cell, normally excluding the lack of a thymus. Exemplary of this type of mammal is the C.B-17 scid/scid mouse, which is believed to be immunoincompetent because of lack of functional recombination, e.g. a non-functional recombinase. However, any genetic defect in progenitor cells which results in the inability of the T cell to mature would be useful. Of particular interest are transgenic mammals, where the immunodeficiency is introduced by integrative recombination, particularly homologous recombination.

The liver tissue and thymus tissue are both used as solid tissue. The two tissues are placed substantially contiguously. The liver tissue is found to amplify, differentiate and mature with discrete subanatomic locations of the growing human fetal thymus, as evidenced by collections of cells of various hematopoietic lineages and stromal cells. The type, quantity and spatial organization of these hematopoietic and stromal cells is similar to that found in normal human bone marrow. Thus, these "bone marrow equivalents" are found to include immature blast cells, cells of the myelomonocytic lineage, cells of the megakaryocytic lineage, cells of the lymphoid lineage, immature adipocytes and undefined stromal cells. These bone marrow equivalents remain functional for periods of at least about 12 months or more.

While any vascularized convenient site for implantation may be employed, of particular interest is the renal capsule, which provides a sanctuary for the tissue. Other sites include the splenic capsule, various subcutaneous locations and the intraperitoneal cavity. Methods of inserting tissue into the renal capsule have been described in the literature and are substantially described in EPA 88.312222.8, filed Dec. 22, 1988.

The tissue will generally be slices of a size in the range of about 0.5–6 mm, more usually 2–5 mm, with a thickness in the range of about 1–2 mm for implantation with a 15- to 20-gauge trocar. Generally, the fetal tissue will be of an age in the range of at least about 7 gestational weeks (g.w), generally about 9–24 g.w. Liver tissue will generally be of an age from about 10–24 g.w., while the age of the thymus tissue will generally be from about 9–24 g.w., more usually less than about 20 g.w.

Other fetal tissue may also be present, particularly bone or bone marrow, where the tissue may also serve as a source of cells to analyze the effect of the infection. The fetal bone will usually be of a size of about 2–5 mm in diameter and 1–20 mm in length, and of an age in the range of about 15–24 g.w.

The tissue to be used may be fresh or frozen tissue (–70° C.), normally frozen within 12 hours of collection. The frozen tissue may be stabilized with suitable preservation agents and DMSO may be added. The introduction of the tissue will occur with a host at an age of less than about 25% of its normal life span, usually to 20% of the normal life span. With mice, the age will generally be of an age in the range of about 3–10 weeks, more usually about 4–8 weeks.

Infection may be achieved by direct injection of the HIV virus. Usually, the injection will involve at least about $10^2$ infectious units, preferably from about $10^3$ to $10^5$ infectious units of HIV. The HIV may be a clinical isolate, a cloned clinical isolate, a genetically modified isolate, or the like. The HIV should not have been cultured in tissue culture for an extended period.

The administration of the drug may begin prior to, substantially concomitant with, or subsequent to the administration of the infectious dose of HIV. Usually, administration of the drug will begin not earlier than 7 days prior to infection, more usually not more than about 1 day prior to infection. Usually, administration of the drug will begin not later than about 7 days after infection, more usually not later than about 1 day after infection. However, after initial screening, different periods of time may be of interest in establishing the effectiveness of the drug in suppressing HIV-induced thymocyte depletion.

The manner of administration will vary greatly, depending upon the nature of the drug. It may be provided orally, ad libitum, intraperitoneally, intravascularly, subcutaneously, intrathymically, or the like. Usually, different dosage levels will be employed, based on past experience with the drug, anticipated levels with human treatment, toxicity or side effects, and the like.

The effect of the drug may be monitored for any convenient time, usually at least 1 week from the initiation of administration of the drug, more usually at least 2 weeks, and at times for periods as long as 6 weeks or more. Preferably, determinations will be made in the period from about 2–6 weeks.

Various measurements can be made as to the effectiveness of the drug in suppressing HIV-induced thymocyte depletion and in maintaining T lymphopoiesis. By employing flow cytometry (fluorescence-activated cell scanning flow cytometry), one can analyze the CD4 and CD8 profile of the peripheral blood, the cell population in a cell dispersion prepared from the thymic implant, or other human fetal tissue which is present, as appropriate. One may also monitor for the presence of HIV, by monitoring the level of p24 in the peripheral blood or the implant, HIV RNA or portion thereof, or HIV DNA, using the polymerase chain reaction. In addition, one may use histological analysis, employing immunochemistry, for detecting the presence of CD4, CD8 and p24 or other proteins of HIV, which are present in the thymic implant.

Of particular interest is analysis for indications of apoptosis in the infected thymus, as indicated by multiple foci of cells with condensed nuclear material as seen by histologic methods or election microscopy or as determined by methods which can discern a DNA degradation profile consistent with apoptosis. Methods which detect the number of DNA termini, such terminal deoxytransferase labelling, can be used to quantitate the number of apoptotic cells. The assay can be performed on tissue sections or cell suspensions. Details as to the localization of apoptotic cells are determined by in situ labelling protocols, which allow histological examination of the infected area.

More accurate enumeration of apoptotic cells will use cell suspensions. The test cells are permeabilized by any suitable method which maintains integrity of the cell, and allows terminal deoxytransferase (TdT) to enter the cell nucleus. In the presence of free oligonucleotides TdT will non-specifically extend a DNA molecule from any terminus. Apoptosis induces double stranded breaks in chromosomal DNA, thereby increasing the number of termini. The amount of oligonucleotide which is polymerized to the DNA will increase with the number of termini present, and so correlates with the DNA degradation seen in apoptosis. Quantitation can be performed by radioactive labelling and enumeration of bound radioactivity, labelling with fluorescent reagents and enumeration by flow cytometry or fluorescent micrscopy, etc. The cells may also be stained with reagents specific for cell surface markers, such as CD4, CD8, etc., allowing for analysis by flow cytometry of multiple parameters.

Drugs that are found to be effective in the subject screening may then be used in the treatment of humans seropositive for HIV. The patient may be only seropositive, have AIDS-related complex, or have full-blown AIDS. Exemplary of drugs useful in the subject treatment is cyclosporine, involved with inhibition of the IL-2 induced pathway, as well as other cellular pathways.

The amount of drug which is administered will vary with the nature of the drug. For example, cyclosporine A would generally be administered in the range of about 0.2 to 20 mg/kg/day. The determination of how large a dosage to be used may be determined using the small animal model and relating the dosage based on pharmacokinetics, e.g. with equations predictive of interspecies scaling. Usually, the lowest effective dose will be used. The drug may be administered by any convenient route, orally or parenterally, e.g. intravascularly, or by inhalation, depot or the like.

The following examples are offered by way of illustration and not by way of limitation.

EXPERIMENTAL

Example 1

Implantation of Liver and Thymus Fragments.

Whole human fetal liver fragments of a size of about 4 mm×6 mm containing all of the representative cells of this organ (microenvironmental stromal cells, hematopoietic stem cells and their progeny, as well as hepatocytes) were surgically implanted into the renal capsule of SCID mice (C.B-17 scid/scid mice) along with whole human fetal thymus fragments of a size of about 2 mm×2 mm. The fragments were from a fetus of under about 24 gestational weeks.

The tissue was obtained directly in the operating room as fetal parts. Without maintaining strict sterility the parts were taken immediately to a gross dissection room. The identified tissue was dissected out and placed into RPMI 1640 medium with 10% fetal calf serum. The organs were then cut into approximately 1×4 mm for insertion using a 19 gauge trocar. The mice are anesthetized with halothane, a 1 cm incision made to expose the kidney and the tissue introduced by means of the trocar beneath the kidney capsule. The fragments were placed in close proximity so as to be in contact. The mice were allowed to grow over a period of 3–12 months, while maintained on a normal diet using trimethoprim/sulfamethoxazole (40 mg/200 mg per 5 ml of suspension; 0.125 ml of suspension per 4 ml of drinking water per mouse per day). At the end of 3–12 months, the mice were checked and human T cells were found in the peripheral circulation of 50% of the animals. The maintenance of human stem cell self-renewal and differentiation in the SCID-hu mouse requires microenvironmental input from the fetal liver stroma. Histological examination of the implanted fetal thymus showed that, in over 80% of the cases, the fetal liver stroma had grown into the substance of the thymus, setting up a hematopoietic environment virtually indistinguishable from that found in bone marrow itself. Included within these "bone marrow islands" are found immature blast cells (likely to be inclusive of early hematolymphoid precursors), cells of the myelomonocytic lineage including polymorphonuclear granulocytes and eosinophilic granulocytes, cells of the megakaryocytic lineages, cells likely to be within the lymphoid lineage, immature adipocytes, and undefined stromal cells. The continuation of these islands for periods of time lasting over 13 months in the majority of implanted animals indicates that human pluripotent hematopoietic stem cells are present as well. In contrast, when the hematopoietic cells of fetal liver are given alone, in the absence of the stromal cells of the organ, bone marrow equivalents are not seen and T cells are only found in the periphery for a period of time ranging from 4 to 13 weeks.

Example 2

Infection of Human Thymus/Liver Employing Implants with Primary Isolates of HIV.

The following primary isolates and molecularly-cloned isolates of HIV 1 were used: JR-CSF, SM, EW, TY 2.4, Xho, SX-1. A flank incision was made to expose the growing human thymus implant of anesthetized SCID-hu mice. A dose of $10^3$–$10^4$ infectious units based on T.C.I.D.$^{50}$ ON PHA blasts was induced by direct intrathymic inoculation. The mice were then maintained within microisolator cages inside a glove box. At varying time points, various determinations were made.

In general, after test animals were sacrificed, thymus implants were surgically removed. In some instances, portions of tissue were set aside for histological examination. Whole or partial implants were crushed between frosted microscope slides to yield a suspension of thymocytes. ~$10^6$ thymocytes in 50 μl PBS/2% FCS were stained with anti-CD4-FITC and anti-CD8-PE conjugated monoclonal antibodies for flow cytometry analysis. ~$10^6$ thymocytes were suspended in a solution of 0.1% Triton/1% citrate/50 μg per ml propidium iodide in water for 1 hour, washed, and resuspended in PBS/2% FCS for flow cytometry analysis. Propidium iodide intercalates DNA and can be used to assess DNA content within a single cell.

The thymus implants were analyzed using light and electron microscopic analysis of tissue slices; a dramatic increase in apoptotic figures was observed in comparison to infrequent apoptotic figures in uninfected controls. As judged by flow cytometry 3.5–4 weeks post-inoculation, there was a substantial inversion of the CD4/CD8 ratio and a substantial reduction in the absolute number and relative proportion of CD4$^+$ CD8$^+$ thymocytes.

This inversion continued to increase, so that at 4.5–6 weeks, there were very few CD4$^+$ cells as well as CD4$^+$ CD8$^+$ cells. The presence of virus based on the amount of p24 per $10^6$ cells showed a continuous increase from the first week to the third week post-inoculation during the period of observation. The CD4 and CD8 cells were monitored by FACS, determining the CD4 and CD8 populations at 3.5–4 and 4.5–6 weeks. The following table indicates the results.

TABLE 1

Sampling of CD4 and CD8 thymocyte distribution in HIV-infected thymus/liver implants in SCID-hu mice from 3.5 weeks to 6 weeks post-infection.

| STRAIN | | SM | | TY | | EW | | JR-CSF | |
|---|---|---|---|---|---|---|---|---|---|
| weeks post-infection | Control (n = 6) | 3.5–4 (n = 8) | 4.5–6 (n = 10) | 3.5–4 (n = 1) | 4.5–6 (n = 3) | 3.5–4 (n = 2) | 4.5–6 (n = 5) | 3.5–4 (n = 3) | 4.5–6 (n = 2) |
| CD4 + 8− | 10–20% | 5–18% | 3–22% | 5% | 2–9% | 11–12% | 3–20% | 13–18% | 10–12% |
| CD4 + 8+ | 68–86% | 1–22% | 1–24% | 2% | 4–55% | 36–37% | 1–45% | 69–76% | 78–80% |
| CD4 − 8+ | 3–12% | 53–89% | 31–90% | 57% | 29–88% | 46–48% | 29–87% | 9–11% | 9–10% |

Note:
At 3.5–4 weeks post-infection with SM, there is a general reduction in thymus cellularity by 80–98%.
At 4.5–6 weeks post-infection with SM, there is a general reduction in thymus cellularity by 93–99%.
A similar pattern of reduction in thymocyte numbers is observed with the primary isolates TY and EW. However, the number of cases examined are too few to give statistical relevance to this observation.

In addition, the number of cells with the normal (2N) complement of DNA was determined for a control and HIV-SM isolate 2 and 4 weeks post-infection. As compared to controls, at 2 weeks post-infection, a normal thymus had 1.3% of cells containing less than (<2N) the normal complement of DNA, while an infected thymus had 23.6% of cells containing less than (<2N) the normal complement of DNA, and at 4 weeks post-infection, a normal thymus had 3.5% of cells containing less than (<2N) the normal complement of DNA, while infected thymuses had 17.1 and 18.2% of cells containing less than (<2N) the normal complement of DNA. (Note: Thymocytes with <2N DNA may represent loss of cellular DNA as a result of active DNA degradation, an indication of the induction of a pre-programmed cell-death pathway.)

Example 3

Treatment with Cyclosporine A of HIV-infected Implants.

experimental animals at 3 weeks post-infection. Despite high levels of p24 being present in the cells in the thymus, the depletion of CD4 expressing thymocytes was substantially diminished as compared to untreated HIV-infected control mice.

In cyclosporine experiments, osmotic minipumps containing Sandimmune, i.v. (cyclosporine A) were surgically implanted subcutaneously 1 week post infection. The estimated drug delivery rate was ~0.5 μl/hour, or 24 mg/kg/day by continuous delivery. Recovery and processing of thymocytes were as previously described. Implants were examined immunohistologically for expression of vital antigens and for gross morphology. Normal thymic architecture was maintained in cyclosporine-treated animals as compared to the observed destruction of the thymic cortex in untreated animals. Expression of viral antigens was readily observed in both treated and untreated animals. Flow cytometry analysis of CD4 and CD8 profiles, as well as p24 ELISA values for normal, infected and treated, and infected and untreated animals is shown in Table 2.

TABLE 2

Effect of cyclosporin (CsA) treatment on HIV-infection in thy/liv SCID-hu mice.

| Length of Infection | weeks on drug | HIV strain SM | CsA | % thymocyte phenotype | | | p24 levels ng/$10^6$ cells | CD4:CD8) 4:8 ratio |
|---|---|---|---|---|---|---|---|---|
| | | | | CD4 + 8− | CD8 + 4− | CD4 + 8+ | | |
| 3 weeks | — | − | − | 18 | 9 | 73 | 0 | 2.0 |
| 3 weeks | — | − | − | 12 | 5 | 83 | 0 | 2.4 |
| 3 weeks | — | − | − | 10 | 6 | 83 | 0 | 1.7 |
| 3 weeks | 2 | − | + | 10 | 3 | 87 | 0 | 3.3 |
| 3 weeks | 2 | − | + | 9 | 2 | 88 | 0 | 3.6 |
| 3 weeks | 2 | + | + | 7 | 4 | 87 | 1.1 | 1.6 |
| 3 weeks | 2 | + | + | 10 | 8 | 80 | 1.6 | 1.2 |
| 3 weeks | 2 | + | + | 7 | 6 | 85 | 2.3 | 1.2 |
| 3 weeks | — | + | − | 20 | 21 | 52 | 2.7 | 0.9 |
| 3 weeks | — | + | − | 13 | 43 | 26 | 1.2 | 0.3 |

(All 10 animals had implants from the same fetal donor.)
CsA treatment commenced one week post-infection: administered via osmotic mini-pump at 24 mg/kg/day.

Following the above procedure, SCID-hu mice were infected with HIV isolate SM. Cyclosporine A was administered subcutaneously via an osmotic minipump over a period of several weeks. The rate of administration was ~24 mg/kg/day and was commenced at different periods post-inoculation. In a first study, administration was begun one week post-inoculation and continued until termination of Example 4 p24 ELISA Analysis.

~2×$10^6$ thymocytes obtained as described in Example 2 were lysed in 1% Triton/PBS/2% FCS. Supernatants were analyzed by p24 ELISA to assess levels of viral p24 antigen on a "per $10^6$ cell" basis.

TABLE 3

Sampling of thymocyte p24 values from HIV-infected (SM isolate) thymus/liver implants in SCID-hu mice from 1 week to 4 weeks post-infection.

| Length of infection | Number of cases | mean p24 value pg/$10^6$ thymocytes | | Standard deviation | Standard error |
|---|---|---|---|---|---|
| | | (Arithmetic) | (Genomic) | | |
| 7 days | 2 | 0 | 0 | 0 | 0 |
| 13 days | 2 | 212 | 169 | 181 | 128 |
| 14 days | 5 | 707 | 500 | 761 | 340 |
| 17 days | 2 | 1065 | 784 | 1020 | 721 |
| 21 days | 7 | 1491 | 1443 | 427 | 161 |
| 28 days | 8 | 885 | 759 | 479 | 169 |

Example 5

Quantitation of Apoptosis in SCID-hu Thymocytes by TdT Assay After Induction by HIV Infection.

To characterize T cell depletion induced by HIV in SCID-hu mice, a terminal transferase (TdT) dependent assay for apoptotic cells was used to analyze cells for apoptosis. The assays were performed according to the methods described in W. Gorczyca, et al. (1993) *Cancer Research* 53:3186–3192. Briefly, terminal deoxytransferase (TdT) is added to a fomaldehyde fixed (permeabilized) cell suspension in the presence of biotin labelled dUTP. After incubation at 37° for 60 minutes, the cells are washed, and resuspended in a staining mix with FITC conjugated avidin. The standard TdT assay in these experiments uses $Co^{++}$, and can detect both double stranded and single stranded DNA breaks. An alternative assay with $Mg^{++}$ instead of $Co^{++}$ detects only single stranded DNA ends or breaks with 3'-end over-hangs and the TdT enzyme is less active. Quantitation is performed by FACS analysis, and can be combined with antibody staining for the presence of cell surface markers such as CD4 and CD8.

Thymocytes from NL43-infected SCID-hu mice were analyzed with the TdT-FACS assay. About 1 to 2% of cells from uninfected mice show TdT positive signals, probably the results of spontaneous apoptosis during T cell development. Table 4 summarizes the induction of T cell depletion during HIV infection of SCID-hu mice.

TABLE 4

Induction of T cell apoptosis in SCID-hu mice by HIV.

| Weeks post infection | HIV strain | % live cells | % TdT+ | p24[a] | HIV DNA by PCR Analysis | CD4/ CD8 ratio |
|---|---|---|---|---|---|---|
| 2 | MOCK | 85 | 1.3 | 0.0 | – | 1.5 |
|   | NL4.3 | 87 | 3.4 | 119.7 | + | 1.5 |
|   | NL4.3 | 79 | 5.1 | 158.1 | + | 1.5 |
| 3 | MOCK | 75 | 2.0 | ND | ND[b] | 1.5 |
|   | NL4.3 | 50 | 80.0 | ND | ND | 1.1 |
|   | NL4.3 | 50 | 53.0 | ND | ND | 0.5 |
|   | NL4.3 | 57 | 22.0 | ND | ND | 1.5 |
| 4 | NL4.3 | 30 | 56.0 | ND | ND | 0.5 |
|   | NL4.3 | 30 | 42.0 | ND | ND | 0.3 |
|   | NL4.3 | 11 | 77.0 | ND | ND | 0.25 |
| 4 | MOCK | 85 | 1.3 | 0.3 | – | 2.3 |
|   | NL4.3 | 10 | 35.0 | 137.3 | + | 0.5 |
|   | NL4.3 | 15 | 21.0 | 218.6 | + | 0.2 |
| AZT[c] | NL4.3 | 82 | 4.7 | 282.2 | + | 1.3 |
| AZT | NL4.3 | 78 | 4.2 | 3.3 | – | 2.6 |
| AZT | NL4.3 | 89 | 0.9 | 6.2 | + | 1.4 |
| 6 | MOCK | 75 | 2.9 | 0.0 | – | 1.1 |
|   | JRCSF | 72 | 0.3 | 180.6 | + | 2.0 |
|   | JRCSF | 60 | 0.4 | 210.3 | + | 1.5 |
|   | HXB2 | 65 | 0.4 | 0.0 | – | 1.3 |
|   | HXB2 | 70 | 2.7 | 0.0 | – | 1.1 |

[a]pg/10^6 thymocytes.
[b]ND, not done.
[c]AZT was applied 1 week and 1 hr before HIV infection.

At two weeks post infection, about 4% of thymocytes have become apoptotic (i.e. TdT positive). No apparent T cell depletion is detected at this stage. About 25–80% of thymocytes become apoptotic at 3 or 4 weeks post infection, depending on the degrees of T cell depletion. Each population of thymocytes (CD4 and/or CD8) appeared to be affected. AZT prevented T cell depletion and decreased the number of TdT positive cells, although HIV replication is still positive. SCID-hu mice infected with the HIV strains JRCSF or HXB2 at 6 weeks post infection were also analyzed. HXB2 infected mice showed no p24 protein and no HIV proviral DNA by PCR. JRCSF infected mice showed levels of p24 almost as high as NL4.3-infected thymuses at 4 wpi and HIV proviral DNA was detected. However, TdT assay showed no signaficant TdT signals in 2 mice infected with either JRCSF or HXB2. A third mouse infected with HXB2 showed some TdT activity and T cell depletion although no p24 nor HIV DNA was detected. It was probably due to nonspecific thymus graft failure.

Example 6

TdT-IS (in situ) Detection of Apoptotic Cells in Tissue Sections.

To identify and characterize apoptotic cells during HIV infection of SCID-hu, the TdT assay was also applied to thymus sections by immunohistochemistry. This assay is less sensitive than the TdT-FACS. In normal mouse thymus, only a few thymocytes at the cortical regions were positive. In HIV infected thymus from SCID-hu, some medullar as well as conical T cells were $TdT^{hi}$ and others showed low TdT signals. A thymus from an uninfected SCID-hu only showed a few TdT positive T cells in the conical region.

It is evident from the above results, that a valuable diagnostic tool is provided for evaluating drugs as to their ability to inhibit the depletion of CD4 expressing cells in the thymus in the presence of HIV infection. In this way, substantial protection of seropositive individuals may be provided, which can only enhance the quality of life for infected individuals, and may also extend their life time. In addition, drugs may now be used in the treatment of HIV-infected individuals to maintain the CD4-expressing population to provide for immune protection of the host.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for screening therapeutic agents for effectiveness in preventing HIV mediated apoptotic thymic depletion of $CD4^+$ or $CD4^+$ $CD8^+$ thymocytes said method comprising:

administering a compound of interest in at least one dosage to a chimeric immunocompromised mouse comprising:

a scid/scid mouse host having an implant comprising human fetal liver and fetal thymus substantially contiguous to provide a bone marrow equivalent tissue, which bone marrow equivalent tissue remains functional for periods of at least about 12 months, and is infected with HIV; and analyzing said bone marrow equivalent or the blood of said mouse host for the effect of said compound on the presence of human CD4$^+$ T cells or CD4$^+$ progenitor cells thereof.

2. A method according to claim 1, wherein said implantation is under the renal capsule.

3. A method according to claim 1, wherein said fetal tissue is of an age of from about 9 to 24 g.w.

4. A method according to claim 1, wherein said analyzing is for the presence of CD4$^+$ T cells h the peripheral blood.

5. A method for treating an HIV seropositive human to suppress thymocyte depopulation of the thymus, said method comprising:

administering an effective dosage of a compound characterized by suppressing thymocyte depopulation in a method for screening therapeutic agents for effectiveness in preventing HIV-mediated thymic depletion of CD4$^+$ or CD4$^+$ CD 8$^+$, employing a chimeric immunocompromised mouse host comprising a scid/scid mouse having an implant comprising human fetal liver and fetal thymus substantially contiguous to provide a bone marrow equivalent tissue, which bone marrow equivalent tissue remains functional for periods of at least about 12 months, and is infected with HIV said method comprising:

administering to said mouse host a compound of interest in at least one dosage; and analyzing said bone marrow equivalent or the blood of said mouse host for the effect of said compound on the presence of human CD4+ T cells or CD4+ progenitor cells thereof.

6. A method according to claim 5, wherein said compound is cyclosporine A.

7. A method according to claim 1, wherein said scid/scid mouse host is a C.B-17 scid/scid.

* * * * *